US005388579A

United States Patent [19]
Dowd et al.

[11] Patent Number: 5,388,579
[45] Date of Patent: Feb. 14, 1995

[54] FETAL ELECTRODE PRODUCT WITH CHANNELED DRIVE MECHANISM AND IMPROVED TORQUE CHARACTERISTICS

[75] Inventors: Edward Dowd, Mallorytown; Joseph O'Neill, Gananoque, both of Canada; David M. DiSabito, Clarence, N.Y.; James R. Hubbard, Lumberton; Cleatis A. Eichelberger, Delran, both of N.J.

[73] Assignee: Graphic Controls Corporation, Buffalo, N.Y.

[21] Appl. No.: 126,218

[22] Filed: Sep. 23, 1993

[51] Int. Cl.$^6$ .......................................... A61B 5/0448
[52] U.S. Cl. .................................... 128/642; 439/909
[58] Field of Search ............... 128/632, 633, 634, 635, 128/666, 642, 783, 784, 785, 786, 639, 640, 641; 439/909

[56] References Cited

U.S. PATENT DOCUMENTS

| | | |
|---|---|---|
| Re. 28,990 | 10/1976 | Hon et al. . |
| Re. 32,204 | 7/1986 | Halvorsen . |
| 3,580,242 | 5/1971 | La Croix . |
| 3,800,800 | 4/1974 | Garbe et al. . |
| 3,827,428 | 8/1974 | Hon et al. . |
| 3,910,271 | 10/1975 | Neward . |
| 4,080,961 | 3/1978 | Eaton . |
| 4,149,528 | 4/1979 | Murphy . |
| 4,180,080 | 12/1979 | Murphy . |
| 4,254,764 | 3/1981 | Neward . |
| 4,301,806 | 11/1981 | Helfer . |
| 4,320,764 | 3/1982 | Hon . |
| 4,321,931 | 3/1982 | Hon . |
| 4,353,372 | 10/1982 | Ayer . |
| 4,501,276 | 2/1985 | Lombardi . |
| 4,577,635 | 3/1986 | Meredith . |
| 4,644,957 | 2/1987 | Ricciardelli et al. . |
| 4,911,657 | 3/1990 | Berlin . |
| 4,913,151 | 4/1990 | Harui et al. . |
| 4,934,371 | 6/1990 | Malis et al. . |
| 5,012,811 | 5/1991 | Malis et al. . |
| 5,046,965 | 9/1991 | Neese et al. . |

(List continued on next page.)

FOREIGN PATENT DOCUMENTS

| | | |
|---|---|---|
| 0092982 | 2/1983 | European Pat. Off. . |
| 0377432 | 11/1990 | European Pat. Off. . |
| 0484107A1 | 6/1992 | European Pat. Off. . |

OTHER PUBLICATIONS

Corometrics Medical Systems, Inc., Leg Plate for Use with Corometrics Model 115, 116 Fetal Monitors, as offered for sale in Catalog No. 2608DAO, Sep. 1988, 5 pages.

(List continued on next page.)

*Primary Examiner*—Lee S. Cohen
*Assistant Examiner*—Brian M. Green
*Attorney, Agent, or Firm*—Ratner & Prestia

[57] ABSTRACT

A fetal electrode product for transmitting signals indicative of fetal heart rate from a fetus to a monitor. A drive mechanism slides and rotates a holder—to which are attached, at opposite ends, a fetal spiral electrode (FSE) and a reference electrode—to secure the FSE to the fetus. The drive mechanism has a solid drive rod, with at least two regions of different diameter defining the torque versus angular deflection characteristics of the drive rods and a clutch connected to the drive rod and imparting translation and rotation to the holder. The clutch is sufficiently pliable to slip over the reference electrode when the holder resists rotation. The drive rod, a handle, and the clutch are integrally molded together to form the drive mechanism and each has a channel transporting a twisted wire strand, which includes an untwisted length to facilitate removal of the FSE from the fetus, from the electrodes to a connector. The connector has an outside dimension greater than the outside diameter of the drive rod to facilitate handling and smaller than the inside diameter of an annular guide tube so that the guide tube can be pulled over the connector after the FSE is attached to the fetus. The connector also has a plug and grip sized to provide a visual indication of full insertion of the plug into the socket opening of a support plate affixed to the mother and electrically connected to the monitor.

32 Claims, 6 Drawing Sheets

U.S. PATENT DOCUMENTS

| | | |
|---|---|---|
| 5,062,426 | 11/1991 | Ulbrich et al. . |
| 5,104,388 | 4/1992 | Quackenbush . |
| 5,135,006 | 8/1992 | Bellinson . |
| 5,168,876 | 12/1992 | Quedens et al. . |
| 5,199,432 | 4/1993 | Quedens et al. . |
| 5,205,288 | 4/1993 | Quedens et al. . |
| 5,215,090 | 6/1993 | Hon et al. . |

OTHER PUBLICATIONS

Edward H. Hon, M.D., "Instrumentation of Fetal Heart Rate, and Fetal Electrocardiography," *American Journal of Obstetrics & Gynecology*, at pp. 772–784 (Jul. 15, 1963).

Berkeley Bio–Engineering, "Operating the Berkeley 900 Fetal Monitoring System" (1975; Revised Feb. 23, 1977).

Edward H. Hon et al., "Electronic Evaluation of Fetal Heart Rate," *Obstetrics & Gynecology*, vol. 40, No. 3, at pp. 362–365 (Sep. 1972).

Information Sheet, Medi-Trace Fetal ECG Electrode, Graphic Controls Canada Limited (Jun. 1984).

Packaging for Spiral Electrode Manufactured by LIT Ltd. for Advanced Medical Systems, Inc. Publicly Available at least since Feb. 1992.

"Medi-Trace Disposable Patient Monitoring Systems" publication of Graphic Controls Corp. Ontario Canada, Aug. 1990.

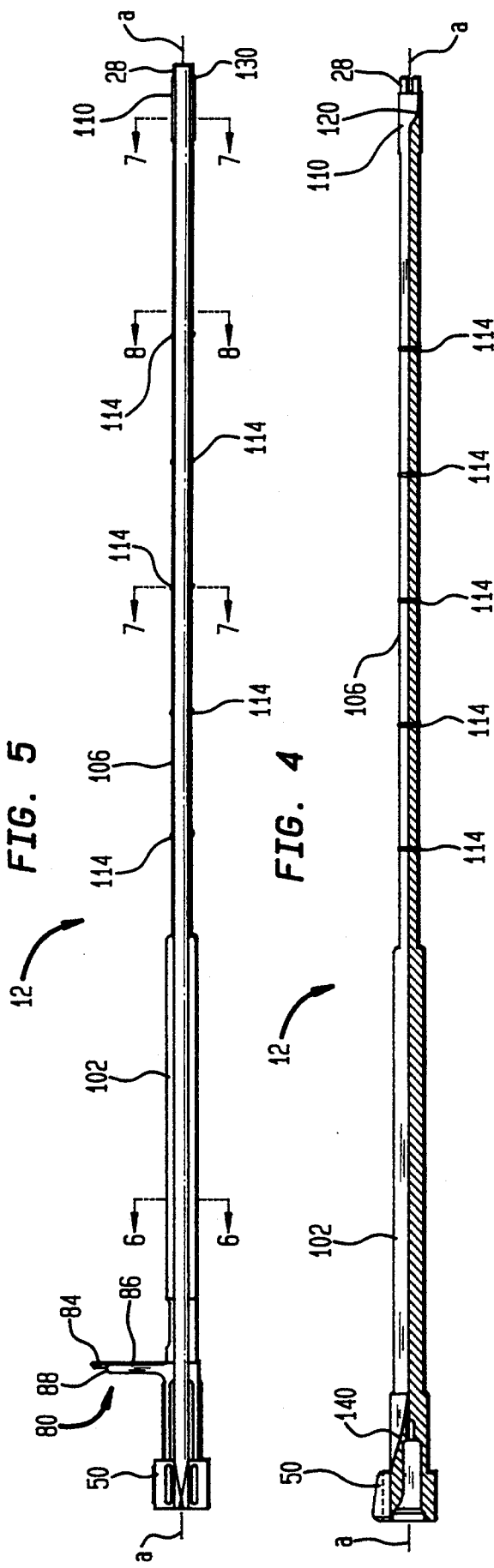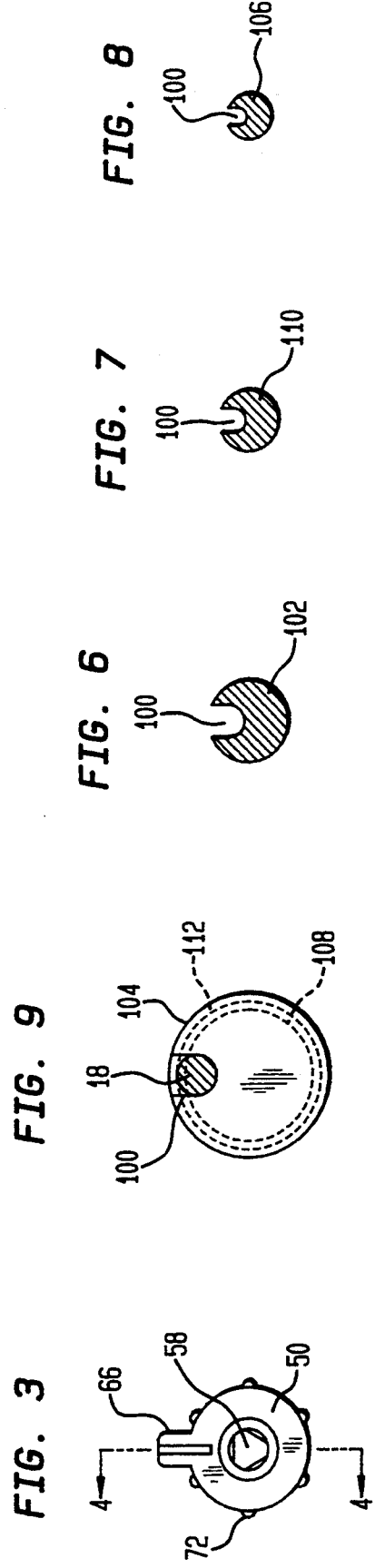

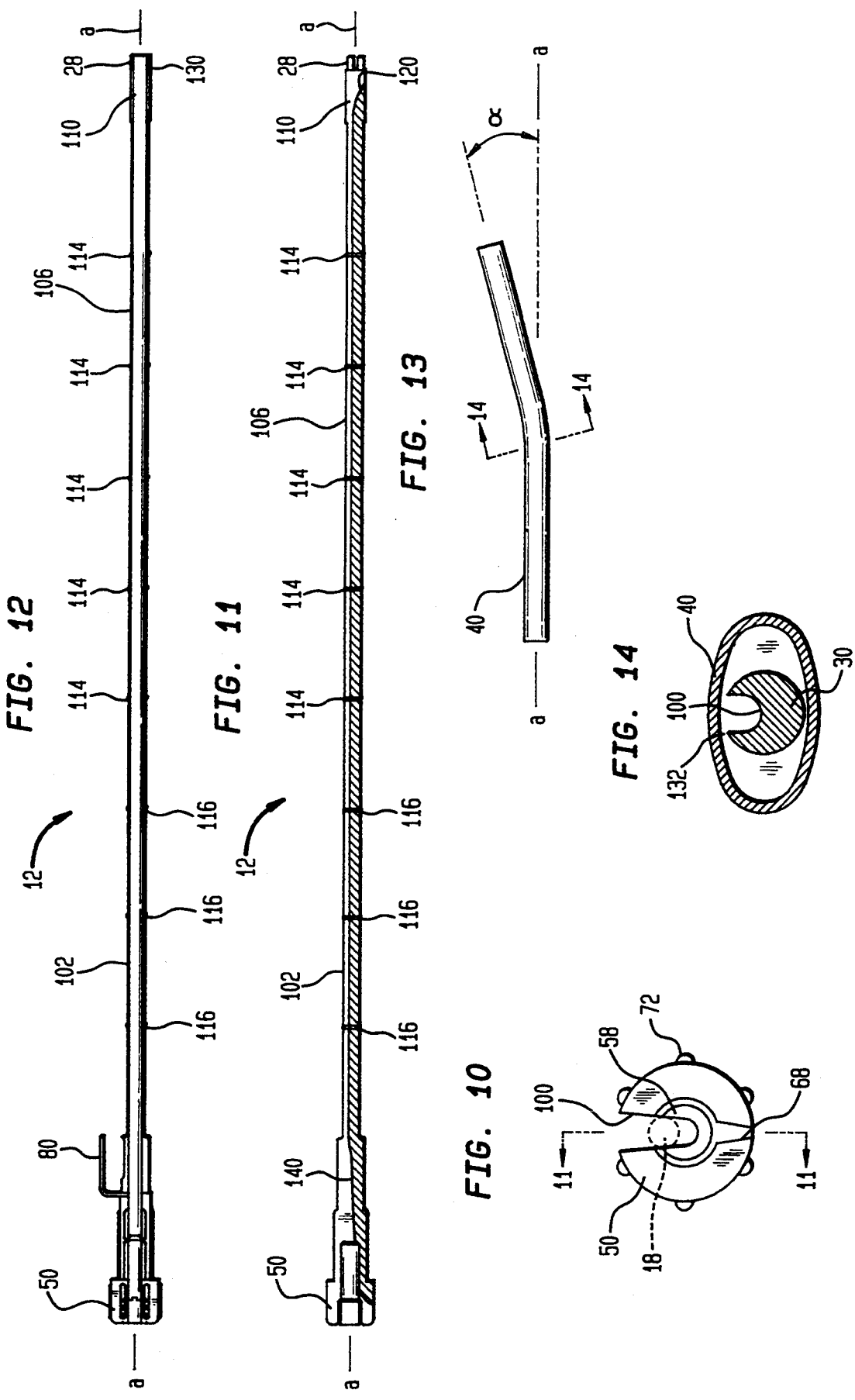

FETAL ELECTRODE PRODUCT WITH CHANNELED DRIVE MECHANISM AND IMPROVED TORQUE CHARACTERISTICS

BACKGROUND OF THE INVENTION

1. Field of the Invention

The present invention relates to a fetal electrode and, in particular, to a fetal spiral electrode which includes a drive rod, a clutch, a handle, and a safety clip integrally molded together to form a channeled drive mechanism for imparting the torque required to attach the electrode to the fetus.

2. Description of the Related Art

It is desirable to monitor fetal heart rate continuously during labor and delivery in order to detect fetal distress. Devices which are external to the mother's body do not adequately isolate the fetal and maternal heartbeats. Consequently, devices which attach directly to the fetus during labor are now commonly used. U.S. Pat. No. Re. 28,990, issued to Hon et al., discloses a fetal spiral electrode (FSE) assembly commonly used to monitor fetal heart rate during birth.

The conventional fetal spiral electrode assembly includes a curved guide tube of adjustable shape for insertion of the fetal spiral electrode through the mother's cervix and into contact with the fetus during labor. A plastic tip or holder is slidably received in the guide tube. A sharp, pointed, fetal spiral electrode is mounted on the forward end of the holder for contacting the fetal epidermis.

A reference (maternal) electrode in the form of a flat fin or plate is electrically isolated from the fetal electrode and located on the rear end of the holder. A flexible, hollow drive tube with a cutout on its forward end fits inside the guide tube and engages the holder. The cutout of the drive tube engages the reference electrode in the holder to impart translation and rotation to the holder and, hence, to the fetal spiral electrode. A handle on the opposite end of the drive tube allows the user to push, pull, and rotate the drive tube within the guide tube. A forward-twisting force is applied to the drive tube to affix the fetal spiral electrode in the fetal epidermis.

The two electrodes are connected to separate wires, which are threaded through the common center of the drive and guide tubes until they ultimately exit at the proximal end of the drive tube. After the fetal spiral electrode is secured to the fetal epidermis, the drive tube and guide tube are removed by pulling the tubes longitudinally over the wires and away from the mother. Removal of the drive and guide tubes leaves the electrodes, the holder, and the wires in place inside the mother. The uninsulated ends of the wires opposite the electrodes are then connected to a fetal monitor.

Manual connection of the uninsulated ends of the wires is cumbersome and risks shorting the wires. If shorted, the wires cannot transmit correct signals from the fetal and reference electrodes. Accordingly, a connector can be added to the fetal spiral electrode assembly disclosed in the '990 patent. As taught by U.S. Pat. Nos. 5,205,288 (issued to Quedens et al.), No. 5,199,432 (issued to Quedens et al.), and No. 5,168,876 (issued to Quedens et al.), the connector solves the problem of manual connection of the uninsulated ends of the wires. Because the guide and drive tubes are removed by pulling them longitudinally over the wires and connector, however, the connector must have an outer dimension which is smaller than the inside diameter of the drive tube (and, of course, the larger-diameter guide tube as well).

The wire connected to the fetal spiral electrode and the wire connected to the reference electrode form a twisted wire strand which enters the connector through a strain relief element. The wire from the fetal spiral electrode is connected to a first, gold, terminal or ring contact; the wire from the reference electrode is connected to a second, gold, terminal or ring contact. The terminals are electrically and physically separated by a spacer. The connector has a forward tapered tip.

The connector engages a support plate, which is affixed to the expectant mother (typically to the thigh) and provided to support the connector. Upon insertion of the connector into an opening of the support plate, the two ring contact terminals on the connector click into physical and electrical contact with two corresponding barrel contacts in the support plate. Moreover, the tip of the connector abuts a wall in the support plate to prevent over-insertion of the connector.

The support plate carries its own ground electrode. Consequently, three electrical circuit paths are created upon engagement of the connector with the support plate: (a) fetal electrode to a first wire to a first contact terminal to a first barrel contact to a first output terminal to the monitor; (b) reference electrode to a second wire to a second contact terminal to a second barrel contact to a second output terminal to the monitor; and (c) ground electrode to a third output terminal to the monitor.

To use the fetal spiral electrode product having a connector, the shape of the guide tube is adjusted and the guide tube is inserted through the mother's cervix and into contact with the fetus. Care must be exercised to assure that the sharp fetal spiral electrode does not extend out of the guide tube during insertion; otherwise, risk to the patient of injury and infection arises. Once the guide tube contacts the fetus (and is held against the fetus using one of the user's hands), the drive tube is advanced (using the second hand) until the fetal spiral electrode contacts the fetus.

While pressure is maintained against the fetus by the guide tube and drive tube, the drive tube is rotated, using the second hand and the handle, until the fetal spiral electrode is secured to the fetal epidermis. Typically, one full revolution suffices to secure the fetal spiral electrode. Then the drive tube and guide tube are removed, leaving the electrodes, the holder, and the wires in place inside the mother, by sliding them over the electrode wires and connector. Finally, the connector is plugged into the support plate.

The connector must be fully inserted into the support plate to assure optimal signal quality. The connector of the conventional device has a constant diameter along its length. The device cannot provide any visual assurance, therefore, that the connector has been fully inserted. This is one drawback of the conventional device.

A second drawback associated with the conventional fetal spiral electrode assembly described above is the potential for the fetal spiral electrode to extend out of the guide tube, during storage or transportation, before the fetal spiral electrode assembly is ready for use. If exposed, the sharp fetal spiral electrode can pierce the package, typically a paper and plastic pouch, in which the assembly is stored and transported. A person handling the electrode (or the patient) may then be harmed and sterilization of the electrode is jeopardized. In addition, the electrode itself may be damaged.

A related problem associated with the fetal spiral electrode assembly described above is the potential for the fetal spiral electrode to extend out of the guide tube during the initial stages of use. Such premature extension may injure the patient and may cause infection. The problem of premature extension of the fetal spiral electrode out of the guide tube, before or during the initial stages of use, has been solved by the packaging system disclosed in co-pending U.S. patent application Ser. No. 08/126,222, filed on Sep. 23, 1993, entitled "Packaging System for a Fetal Electrode" and incorporated herein by reference.

Another problem associated with the conventional fetal spiral electrode assembly is that the wires and the connector, which convey the electrical signal from the fetus to the monitor, must traverse laterally through the hollow center of the drive tube. This means that the connector necessarily must have an outer dimension smaller than the internal diameter of the guide and drive tubes. Because the guide and drive tubes must be small in diameter in order to transit the closed cervix, this, in turn, means that the connector diameter must be relatively small.

The requirement of a small-diameter connector has several disadvantages. First, the clinician must grasp and handle the connector to insert it into the corresponding socket of the support plate. The smaller the connector, the more difficult it is to handle. Second, a proper connection of the connector to the support plate must be ensured. A smaller connector of constant cross-section is unable to provide assurance that the required connection has been achieved. Finally, the support plate and fetal spiral electrode operate in a fluid-filled environment. A smaller connector risks an inadequate seal of the opening in the support plate into which the connector is inserted. Absent an adequate seal, fluid from the environment may enter the opening in the support plate and adversely affect the connector-socket electrical connection or the other electrical circuit paths discussed above.

U.S. Pat. No. 4,644,957 recognizes the drawback, that the connector must necessarily be of a diameter smaller than the guide and drive tubes, characteristic of the fetal spiral electrode assembly described in the '990 patent. The '957 patent solves that problem by placing the wires alongside a solid drive wrench (rather than inside an annular drive tube) and by providing a slotted guide channel with a C-shaped cross-section (as opposed to a solid, annular guide tube). The wires reside freely inside the guide channel and parallel to the drive wrench. Because the wires are of a smaller diameter than the width of the longitudinal slot in the guide channel (enabling the wires to exit the slot), they must either be wound in a spiral around the drive wrench or positioned in the guide channel away from the slot to retain them securely inside the guide channel. After the fetal spiral electrode is secured to the fetus, the drive wrench is pulled out of the drive channel. The guide channel is then withdrawn, in a similar manner, as the wires slip freely out of the longitudinal slot in the guide channel.

The solution presented by the '957 patent has its own difficulties. The wires must be sized so that they are smaller than the width of the longitudinal slot in the guide channel. Thus, the size of the wires is restricted and the wires may exit the slot prematurely. More importantly, the wires reside freely inside the guide channel and may affect rotation of the drive wrench. The wires may become entangled around the drive wrench, in the worst case, preventing both rotation and removal of the drive wrench. The risk of entanglement is especially great if the wires are purposefully wound in a spiral around the drive wrench. Finally, the wires may not be aligned with the slot, after the drive wrench is removed, rendering withdrawal of the guide channel difficult.

Still another problem associated with the fetal spiral electrode assembly described in the '990 patent is that the drive mechanism consists of the handle and a separate drive tube. The plastic, molded handle is pressure-fit onto the extruded drive tube. When the user rotates the drive handled it is assumed that the drive tube rotates by the same amount as the drive handle and that the holder and fetal spiral electrode, in turn, rotate commensurately. The pressure fit of the conventional two-piece drive mechanism may inadequately transmit rotational motion between the handle and the drive tube; some slippage may occur. If so, the drive tube rotation (and, therefore, the fetal spiral electrode rotation) will not directly reflect the handle rotation.

The two-piece drive mechanism also fails to provide the user with consistent and optimal tactile feedback. The user of the fetal spiral electrode assembly described above turns the drive handle until a mild resistance is felt. Such resistance indicates that the fetal spiral electrode has been securely attached to the fetus. Because slippage may occur between the handle and the drive tube through the pressure fit of the conventional two-piece drive mechanism, the user may not receive the tactile feedback desired. Consequently, the user lacks confidence that a secure attachment of the fetal spiral electrode has been achieved.

Still another problem associated with the conventional fetal spiral electrode assembly is that the electrode wires must be straightened completely before the guide and drive tubes are pulled over the wires and connector. Otherwise, the wires may drag, catch, or snag on the drive tube, as it is removed, placing tension on the fetal spiral electrode. Such tension may pull the fetal spiral electrode out of engagement with the fetus.

Graphic Controls Canada Limited sold a fetal ECG electrode product during the mid 1980's in Canada, under the MEDI-TRACE ® trademark, which incorporated a slotted drive rod to eliminate routing of the wires through a hollow drive tube. The open slot in the drive rod provided for a clean release of the electrode wires after attachment of the fetal spiral electrode, thus reducing wire friction and tugging during removal of the drive rod.

The product was unsuccessful, in part, because the solid, slotted drive rod was inflexible (too rigid and stiff) in comparison to its hollow tube counterpart. The stiffness of a drive rod in a fetal spiral electrode assembly must balance competing requirements. First, the stiffness must be sufficient to (a) transmit torque directly from the handle to the holder and fetal spiral electrode, (b) provide the "feel" required to assure that the fetal spiral electrode is attached to the fetus without over-rotation which would risk damage to the fetal scalp, and (c) allow sufficient bend so that the fetal spiral electrode can be inserted comfortably into the mother.

The Canadian product was overly stiff (insufficiently flexible) and, accordingly, failed to provide the feel required to avoid over-rotation. Consequently, the product risked fetal injury: pulling a plug of skin out of the fetus upon over-rotation of the handle. The clinician was required, therefore, to exert the utmost care to avoid over-rotation.

The risk of injury presented by the Canadian product might have been reduced by a clutch mechanism at the interface between the drive rod and the holder. Such a mechanism would transmit a torque sufficient to affix the fetal spiral electrode to the fetus but slip, or disengage, if a larger torque were applied. The Canadian product did not have such a protective mechanism. In short, therefore, the Canadian product was unsuccessful because it was unable to achieve the same torque characteristics as its conventional, hollow, drive tube counterpart.

SUMMARY OF THE INVENTION

The present invention is embodied in a fetal electrode product for transmitting signals indicative of fetal heart rate from a fetus to a monitor. The product has a holder made of an insulating material to which are attached, at opposite ends, a fetal spiral electrode and a maternal reference electrode. A twisted wire strand includes a pair of wires respectively connecting the fetal spiral electrode and the maternal reference electrode to a connector. The twisted wire strand includes an untwisted length to facilitate removal of the fetal spiral electrode from the fetus.

A drive mechanism slides and rotates the holder to secure attachment of the fetal spiral electrode to the fetus. The drive mechanism has (a) a solid drive rod with at least two regions of different diameter defining the torque versus angular deflection characteristics of the drive rod, (b) a handle connected to the drive rod and imparting translation and rotation to the drive rod, and (c) a clutch connected to the drive rod and imparting translation and rotation to the holder. The drive rod, handle, and clutch are integrally molded together to form the drive mechanism. Each of the drive rod, handle, and clutch has a channel transporting the twisted wire strand from the electrodes to the connector.

The clutch has a pair of arms defining a pair of slots releasably engaging and centering the maternal reference electrode for transmitting torque between the drive rod and the holder. The arms are sufficiently pliable to slip over the maternal reference electrode when the holder resists rotation. Resistance occurs when the fetal spiral electrode is attached to the fetus.

The product includes an annular guide tube sized to be comfortably inserted through the cervix of a mother in labor. The connector has an outside dimension greater than the outside diameter of the drive rod to facilitate handling and smaller than the inside diameter of the annular guide tube so that the guide tube can be pulled over the connector after the fetal spiral electrode is attached to the fetus.

A support plate is affixed to the mother and has a housing and two terminals, electrically connected to the monitor, within a socket opening in the housing. The connector has a plug of a predetermined length with two contacts spaced from each other. When the connector is inserted fully into the socket opening of the support plate, the contacts engage the terminals. The connector also has a grip of larger diameter than the plug. A shoulder is provided between the plug and the grip and abuts the housing of the support plate when the connector is fully inserted into the socket opening.

BRIEF DESCRIPTION OF THE DRAWINGS

FIG. 3 is an end view of the first (and preferred) embodiment of the drive mechanism in accordance with the present invention;

FIG. 4 is a cross-sectional view taken along the line 4—4 of FIG. 3;

FIG. 5 is a side view of the first embodiment shown in FIGS. 3 and 4;

FIG. 6 is a cross-sectional view taken along the line 6—6 of FIG. 5;

FIG. 7 is a cross-sectional view taken along either of the lines 7—7 of FIG. 5;

FIG. 8 is a cross-sectional view taken along the line 8—8 of FIG. 5;

FIG. 9 is a cross-sectional view of the drive rod of the first embodiment of the drive mechanism of the present invention, illustrating the three regions of varying diameter of the drive rod;

FIG. 10 is an end view of the second embodiment of the drive mechanism in accordance with the present invention;

FIG. 11 is a cross-sectional view taken along the line 11—11 of FIG. 10;

FIG. 12 is a side view of the second embodiment shown in FIGS. 10 and 11;

FIG. 13 is a side view of the conventional guide tube used in combination with the fetal spiral electrode system in accordance with the present invention, illustrating a typical bend angle;

FIG. 14 is a cross-sectional view taken along the line 14—14 of FIG. 13;

DETAILED DESCRIPTION OF THE INVENTION

A. Overview of the Invention

Figure 1:
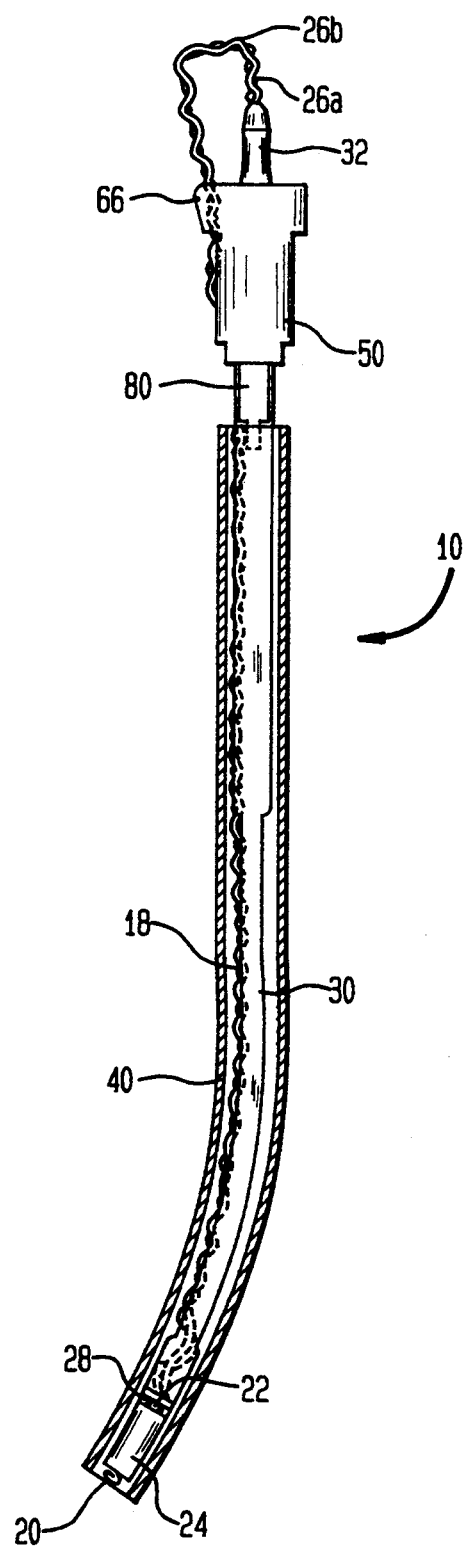
FIG. 1 is a side view of an exemplary fetal spiral electrode system in accordance with the present invention (with the conventional guide tube shown in cross section)

FIG. 1 shows a side view of an exemplary fetal spiral electrode system 10 in accordance with the present invention. Electrode system 10 includes a sharp, pointed fetal spiral electrode 20 for contacting the fetal epidermis; a reference (maternal) electrode 22 in the form of a flat fin or plate which is electrically isolated from fetal spiral electrode 20; a holder 24; and two electrode wires 26a and 26b.

Holder 24 is an electrically insulating plastic and is adapted to be slidably received inside a guide tube 40. Fetal spiral electrode 20 is mounted on the forward end of holder 24. Reference electrode 22 is attached to the rearward end of holder 24.

Guide tube 40 is a curved, form-sustaining member of adjustable shape for insertion of fetal spiral electrode 20 through the mother's cervix and into contact with the fetus during labor. Guide tube 40 can be manufactured via a standard extrusion process which forms the hollow, tubular shape. Any material which is flexible, form-sustaining, and compatible with insertion into the body is suitable for guide tube 40. Polyethylene is preferred. Guide tube 40 has a length of about 280 mm (11 inches), a substantially uniform outer diameter of about 8 mm (0.3 inches), and a substantially constant wall thickness of about 1 mm (0.04 inches). Guide tube 40 does not have any slots, slits, breaks, or other openings in its surface which might injure the mother or catch wires 26a and 26b.

An integral, flexible drive mechanism 12 is provided (see FIGS. 4, 5, 11, and 12). Drive mechanism 12 includes a drive rod 30 which is slidably received in guide tube 40. Drive rod 30 has a clutch 28 at its forward end. Clutch 28 engages reference electrode 22 in holder 24 to impart translation and rotation to holder 24 and, hence, to fetal spiral electrode 20. A handle 50 on the opposite end of drive rod 30 allows the user to push, pull, and rotate drive rod 30. A safety clip 80 is incorporated on handle 50 to protect fetal spiral electrode 20 in a recessed position (as shown in FIG. 1) inside guide tube 40 before and during the initial stages of use. Drive rod 30, clutch 28, handle 50, and clip 80 are integrally molded together to form drive mechanism 12 of fetal spiral electrode system 10.

Electrode wires 26a and 26b are separately coupled to respective electrodes 20 and 22. Electrode wire 26a (typically green in color) connected to fetal spiral electrode 20 and electrode wire 26b (typically red) connected to reference electrode 22 form a twisted wire strand 18 which extends from electrodes 20 and 22 along the entire length of drive rod 30 and handle 50. A catch 66 is provided near the end of handle 50 opposite drive rod 30. Catch 66 locks wire strand 18 in a fixed position. The ends of wires 26a and 26b opposite holder 24 terminate in a male connector 32.

Figure 2:
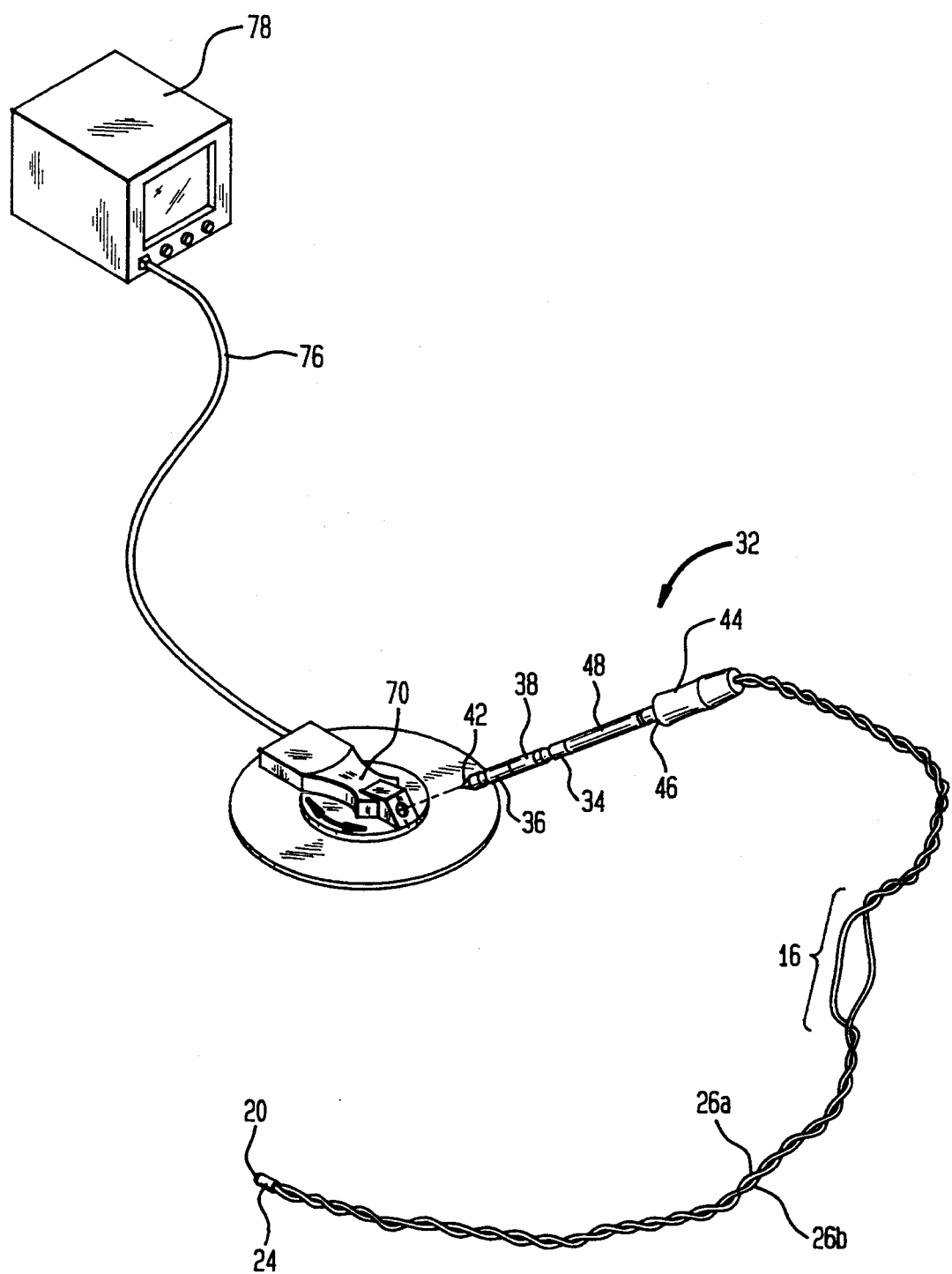
FIG. 2 is a perspective view of the improved electrode wires and connector of the present invention and illustrates those components in combination with several conventional elements.

Turning to FIG. 2, the individual wires 26a and 26b are separately connected to first and second terminal (or ring) contacts 34 and 36 in connector 32. Contacts 34 and 36 are electrically and physically separated by a spacer 38. Connector 32 is designed to be inserted into a support plate 70 which is affixed to the mother (typically to the thigh). Support plate 70 is connected, via a cable 76, to a monitor 78. Insertion of connector 32 in support plate 70 connects electrodes 20 and 22 to monitor 78.

B. Specific Components of the Invention

Having generally described fetal spiral electrode system 10, the individual components of fetal spiral electrode system 10 can now be described in greater detail.

1. Wires 26a and 26b

Each wire 26a and 26b is approximately 1 mm (0.04 inches) in diameter. The length of wires 26a and 26b from maternal electrode 22 and fetal spiral electrode 20, respectively, to connector 32 is about 610 mm (24 inches). This length allows the clinician sufficient "play" to choose placement of support plate 70 on the mother's abdomen or leg at a number of suitable positions.

As noted above and illustrated in FIG. 1, wires 26a and 26b form twisted wire strand 18. Wires 26a and 26b are provided in an untwisted length 16 along a short distance (25-50 mm or 1-2 inches) of wire strand 18. Untwisted length 16 may be located at any point between connector 32 and the point at which wires 26a and 26b engage catch 66 on handle 50.

To remove it from engagement with the fetus, fetal spiral electrode 20 must be rotated counterclockwise. Many clinicians pull wires 26a and 26b apart to facilitate removal of fetal spiral electrode 20 from the fetus. Absent untwisted length 16, the clinician may cut wires 26a and 26b before they are pulled apart. Untwisted length 16 allows the clinician to separate wires 26a and 26b without cutting them. Untwisted length 16 is provided, therefore, close to the point at which wires 26a and 26b engage catch 66 on handle 50. For example, untwisted length may be 180-230 mm (7-9 inches) from connector 32.

2. Connector 32

Wire strand 18 terminates in a connector 32, without need for a strain relief element, and the individual wires 26a and 26b are separately connected to ring contacts 34 and 36 in connector 32. Ring contacts 34 and 36, which are separated by spacer 38 and may be gold-plated to resist corrosion, have grooves to facilitate mechanical and electrical connection to mating barrel contacts in support plate 70 upon insertion of connector 32 into an opening of support plate 70 (shown in FIG. 2). Connector 32 has a forward tapered tip 42 which plugs into a longitudinal passage 58 (see FIGS. 3 and 10) in the end of handle 50 (connector 32 is shown plugged into passage 58 in FIGS. 1 and 18). Moreover, tip 42 of connector 32 abuts a wall in support plate 70 to prevent overinsertion of connector 32.

Connector 32 has a grip 44 with a diameter sufficiently large (specifically, larger than the outer diameter of drive rod 30) and an ergonomically designed shape to permit the user to grasp it easily and to insure a proper, sealed connection of connector 32 to support plate 70. The maximum diameter of connector grip 44 is sufficiently small (specifically, smaller than the inner diameter of guide tube 40), however, to permit the user to slide guide tube 40 over grip 44.

Larger diameter grip 44 of connector 32 renders connector 32 easy to handle, especially with gloved hands. Moreover, the diameter of connector 32 changes, at a shoulder 46, from a smaller diameter plug 48 to larger diameter grip 44. The length of smaller diameter plug 48 is selected to correspond to the length by which connector 32 must be inserted fully into support plate 70 to assure optimal signal quality. Thus, connector 32 permits a visual indication of full attachment of connector 32 to support plate 70.

For purposes of example only, plug 48 has a length of about 20 mm (0.8 inches) and a diameter of about 3 mm (0.1 inches). Grip 44 has a length of about 18 mm (0.7 inches) and a maximum diameter of about 6 mm (0.25 inches). Thus, connector 32 has a length of about 38 mm (1.5 inches) and a maximum diameter of about 6 mm (0.25 inches).

Discussion turns now to the integral, molded components of drive mechanism 12: drive rod 30, clutch 28, handle 50, and clip 80. The drawings illustrates two, alternative embodiments for drive mechanism 12.

FIGS. 3-8 illustrate the first (and preferred) embodiment. FIGS. 10-12 depict the second embodiment of drive mechanism 12.

As shown disposed along longitudinal axis "a" in FIGS. 4, 5, 11, and 12, the length of drive mechanism 12 is about 300 mm (11.8 inches). Drive mechanism 12 is made of polyethylene (high or low density). Polypropylene is also suitable. The combination of structure and flexural modulus in drive mechanism 12 is important to assure that drive mechanism 12 delivers the torque necessary to rotate fetal spiral electrode 20 and provides the "feel" required to assure that fetal spiral electrode 20 is attached to the fetus without over-rotation.

3. Drive Rod 30

Two, alternative embodiments of drive rod 30 are shown in FIGS. 3-9 and 10-12, respectively. Guide tube 40 must be able to bend at least 45°, and preferably 90°, relative to longitudinal axis a, to transit the cervix and place fetal spiral electrode 20 into position against the fetus. Drive rod 30 must bend similarly when positioned inside guide tube 40. Because drive rod 30 is solid and is not an annular tube, the material chosen for drive rod 30 must assure sufficient flexibility.

FIGS. 3-9 illustrate the first (and preferred) embodiment of drive rod 30. Drive rod 30 has three, separate regions along its length to accommodate the variously curved shape of guide tube 40. Specifically, the first region 102 adjacent and integral with handle 50, where the minimum drive rod bending exists because guide tube 40 is relatively straight in this area, has an outer diameter 104 (about 5.5 mm or 0.22 inches) only slightly less than the inner diameter of guide tube 40 (about 6 mm or 0.23 inches). See FIGS. 6 and 9. The second, central region 106, where the drive rod bending is maximum, has a smaller outer diameter 108 (about 4 mm or 0.16 inches) rendering drive rod 30 more flexible. See FIGS. 8 and 9. Central region 106 is about 165 mm (6.5 inches) long. Finally, a short region 110 adjacent clutch 28 is provided with an intermediate outer diameter 112 (about 5 mm or 0.20 inches). See FIGS. 7 and 9. Short region 110 is about 12.5 mm (0.5 inches) long.

Drive rod 30 has a channel 100 which runs longitudinally along its entire length. Channel 100 is sized, having a radius of about 1.2 mm (0.05 inches) and a top opening of about 2.4 mm (0.10 inches), to permit wire strand 18 to exit drive rod 30 through channel 100 when drive rod 30 is removed from guide tube 40. Wire strand 18 has an outer diameter of about 2 mm (0.08 inches). Thus, wire strand 18 slips out of channel 100 without the need for radial expansion of drive rod 30. The depth of channel 100 is sufficient, however, to prevent wires 26a and 26b from exiting channel 100 when drive rod 30 is inside guide tube 40.

Central region 106 of drive rod 30 has a number of journals 114 spaced, at intervals of about 25 mm (1 inch), along its length. Journals have a length of about 1 mm (0.04 inches) and an outer diameter approximately equal to diameter 112 of short region 110 (about 5 mm or 0.20 inches). See FIG. 7. Thus, the diameter of journals 114 is larger than diameter 108 of central region 106.

As shown in FIG. 9, journals 114 have a height sufficient so that wire strand 18, when placed in channel 100, is tangent to the outer diameter of journals 114. The geometrical relationship between journals 114 and the depth of channel 100 provides a simulated cylinder for uniform contact between wires 26a and 26b and the inside wall of guide tube 40. Consequently, smooth, low-friction rotation of drive rod 30 in guide tube 40 is assured regardless of the bend angle assumed by guide tube 40. This is especially important in central region 106 of drive rod 30 where bend of guide tube 40 and drive rod 30 is most pronounced.

Journals 114 each have a notch which corresponds to the width of top opening of channel 100. Removal of drive rod 30 must be accomplished without tugging on wire strand 18. Therefore, the ends of the notches in journals 114 are provided with a radius or chamfer to eliminate sharp edges which might catch wires 26a and 26b as they exit channel 100 of drive rod 30. Untwisted length 16 of wire strand 18 should not be provided along the length of wire strand 18 which must exit channel 100 of drive rod 30; wire strand 18 will exit channel 100 more easily than an untwisted pair of individual wires.

The first embodiment of drive rod 30 described above has three regions of varying diameter. An alternative embodiment of drive rod 30, as shown in FIGS. 10-12, has only two regions of varying diameter. Otherwise, the two embodiments are substantially identical.

In the second embodiment, first region 102 and central region 106 both have an outer diameter 108 of about 4 mm (0.16 inches). Thus, the diameter of first region 102 is smaller in the second embodiment of drive rod 30 than in the first embodiment, rendering the second embodiment more flexible. First region 102 is provided with three additional journals 116, each having an outer diameter of about 5.5 mm (0.22 inches), to facilitate rotation of drive rod 30 in guide tube 40. The two embodiments of drive rod 30 illustrated in the drawings are examples only. The number of regions provided in forming guide rod 30, the diameters of those regions, and the number of journals—all might be varied.

The maximum outer diameter of drive rod 30 for either embodiment is about 5.5 mm (0.225 inches). As shown in FIGS. 13 and 14, this diameter assures a clearance 132 of about 0.025 mm (0.001 inches) between drive rod 30 and guide tube 40 at the smallest statistically projected inside dimension of 0.226 inches when guide tube 40 is bent at an angle alpha of about 45°.

Drive rod 30 transmits torque between handle 50 and clutch 28. The variable shaft flexibility provided by the various regions of drive rod 30 enhances both the ability of the user to push, pull, and rotate drive mechanism 12 and the "feel" of drive mechanism 12 relative to conventional devices containing shafts of uniform rigidity throughout. The various regions of drive rod 30 are designed to control the torque versus angular deflection characteristics of drive rod 30 and, hence, of drive mechanism 12.

Figure 15:
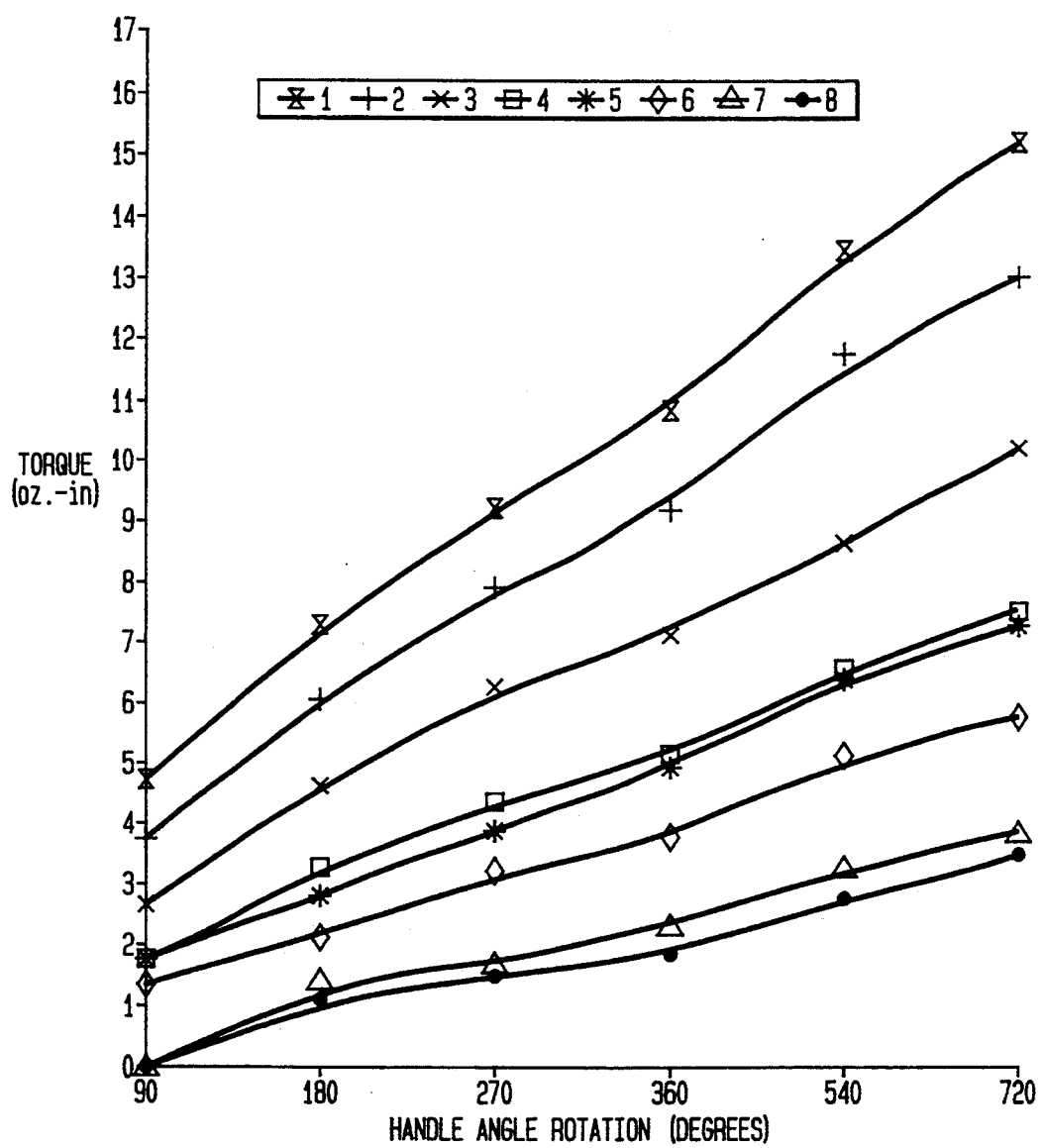
FIG. 15 is a graph of torque (oz. in.) versus handle angle rotation (degrees) for the drive rod of the present invention, as constructed using various materials having different flexure moduli, and for a prior art drive tube.

FIG. 15 is a graph of torque (oz. in.) versus handle angle rotation (degrees) for the preferred embodiment of drive rod 30, as constructed using seven materials (curves labeled 1-4 and 6-8) each having a different modulus of flexure. Curve 5 depicts a prior art drive tube. The torque characteristics of the conventional FSE 2000 product, previously marketed by Graphic Controls Corporation of Buffalo, N.Y. (the assignee of rights to the present invention), are depicted by Curve 5.

The table below summarizes the design, material, and modulus of flexure (in psi) for each of the eight curves shown in FIG. 1.

TABLE

| CURVE | DESIGN | MATERIAL | FLEX. MODULUS |
| --- | --- | --- | --- |
| 1 | Invention | HIMONT PF511 | 130,000 |
| 2 | Invention | DOW 12350N | 121,000 |
| 3 | Invention | DOW 42047N | 110,000 |
| 4 | Invention | DOW 2553 | 80,000 |
| 5 | Prior Art | TENITE 1830E | — |
| 6 | Invention | DOW 2503 | 60,000 |
| 7 | Invention | DOW 2517 | 32,000 |
| 8 | Invention | REXENE 2030 | 14,000 |

HIMONT PF511 is a polypropylene material available from Himont Inc. of Wilmington, Del. The Dow Chemical Company of Midland, Mich. supplied two high density polyethylene products (DOW 12350N and DOW 42047N) and three linear, low density polyethylene products (DOW 2553, DOW 2503, and DOW 2517) tested. REXENE 2030 is a low density polyethylene material available from Rexene Products Company of Odessa, Tex. The FSE 2000 product is made of low density polyethylene sold by Eastman Kodak of Rochester, N.Y. under the designation TENITE 1830E.

FIG. 15 illustrates that the DOW 2553 low density polyethylene material gives the preferred embodiment of drive rod 30 of the present invention a torque versus handle angle rotation curve which is nearly identical to that of the conventional FSE 2000 product. Accordingly, the "feel" of drive mechanism 12 is acceptable when DOW 2553 is used to mold drive mechanism 12; therefore, the DOW 2553 low density polyethylene material is preferred.

The alternative embodiment of drive rod 30 described above, in which first region 102 and central region 106 have the same outer diameter 108 and there are a total of eight journals 114 and 116, represents approximately a 30% reduction in stiffness for drive rod 30. As would be recognized by a person of ordinary skill in the art of drive rod designs the alternative embodiment of drive rod 30 would permit use of a higher modulus material (rather than the DOW 2553 material) yet would still provide the same torque characteristics as the preferred embodiment. Another alternative would be to reduce the diameter of the central region 106 in the preferred embodiment (to decrease the stiffness of drive rod 30) and to use a material having a higher modulus. Obviously, similar torque characteristics can also be achieved by increasing the diameter of central region 106 while using a material having a lower modulus than the DOW 2553 material.

The stiffness of drive rod 30 when constructed of a linear, low density polyethylene, such as DOW 2553, is sufficient to (a) transmit torque directly from handle 50 to clutch 28 (and, hence, to holder 24 and fetal spiral electrode 20), (b) provide the "feel" required to assure that fetal spiral electrode 20 is attached to the fetus without over-rotation which would risk injury to the fetus, and (c) allow drive rod 30 to bend with sufficient flexibility as guide tube 40 bends. In short, therefore, by incorporating predetermined regions and journals of varied diameter to control its torque versus angular deflection characteristics, drive rod 30 has a stiffness which transmits the required torque, provides the required feel, and allows sufficient bend—yet is solid and has channel 100 to permit fetal spiral electrode system 10 to incorporate a larger connector 32.

4. Clutch 28

As shown in FIGS. 4 and 11, drive rod 30 blends into and is integral with clutch 28. A ramp 120 is provided in the transition area between drive rod 30 and clutch 28. Wire strand 18 rests on ramp 120 as it travels from channel 100 (which is above the center-line of drive mechanism 12 in central region 106 of drive rod 30) to the center of clutch 28 where it engages reference electrode 22.

Figure 17:
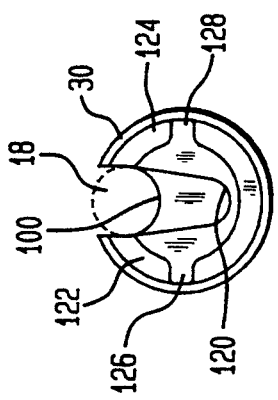
FIG. 17 is an end view of the clutch illustrated in FIG. 16.
Figure 16:
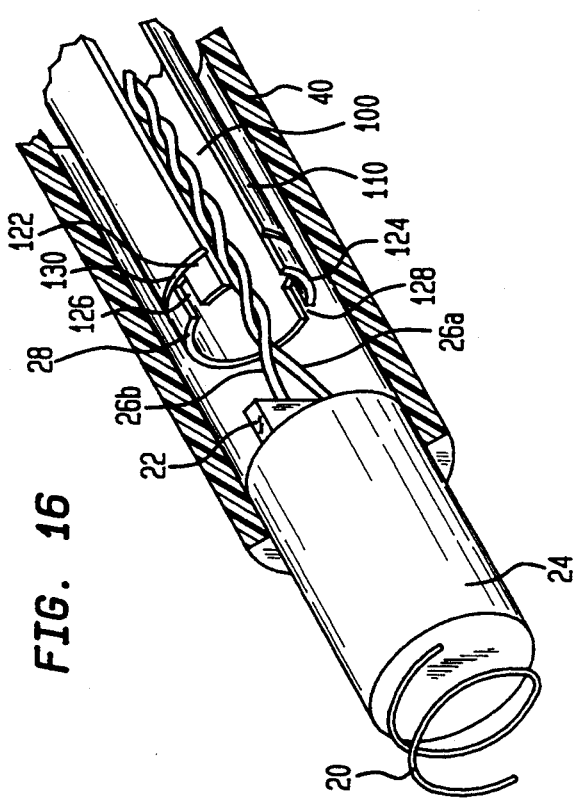
FIG. 16 is a perspective view of the clutch of the fetal spiral electrode system in accordance with the present invention.

FIGS. 16 and 17 best illustrate clutch 28. Clutch 28 has a pair of arms 122 and 124 which define slots 126 and 128. Arms 122 and 124 releasably engage fin-shaped maternal electrode 22, in slots 126 and 128, and center electrode 22 upon engagement. Clutch 28 transmits torque between drive rod 30 and holder 24.

The connection between slots 126 and 128 and electrode 22 is relatively "loose" so that arms 122 and 124 will slip and deflect when holder 24, to which electrode 22 is mounted, meets with a relatively slight amount of resistance to rotation. This occurs when fetal spiral electrode 20 has pierced the fetal epidermis and the front face of holder 24 has contacted the fetus. Continued rotation of handle 50 once resistance has occurred will cause arms 122 and 124 to slip and deflect over electrode 22 and prevent transmission of rotation from handle 50 and drive rod 30 to holder 24 and fetal spiral electrode 20. This loose driving connection is accomplished by making arms 122 and 124 of clutch 28 between slots 126 and 128 soft or pliable enough to allow arms 122 and 124 to bend and slip over electrode 22 when holder 24 resists rotation.

The length of arms 122 and 124 and, correspondingly, the depth of slots 126 and 128 is about 2.5 mm (0.1 inches). Therefore, slots 126 and 128 can fully receive maternal electrode 22 which protrudes out of holder 24 by about 2 mm (0.08 inches). A rim 130 is provided on clutch 28, at the junction between clutch 28 and short region 110 of drive rod 30, for guidance of drive mechanism 12 in guide tube 40.

Clutch 28 will disengage maternal electrode 22 after complete engagement of fetal spiral electrode 20. Thus, clutch 28 is designed to disengage maternal electrode 22 in a relatively narrow range of torque. Clutch 28 gives drive mechanism 12 a protective mechanism, allowing drive mechanism 12 to transmit a torque sufficient to affix fetal spiral electrode 20 to the fetus and to slip, or disengage, if a larger torque is applied.

5. Handle 50

Handle 50 is attached to and integral with first region 102 of drive rod 30. An incline 140 is provided in the transition area between drive rod 30 and handle 50. Wire strand 18 rests on incline 140 as it travels from channel 100 (which is above the center-line of drive mechanism 12 in first region 102 of drive rod 30) either to a slit 68 in the side of handle 50 (see FIG. 10) or to external catch 66 (see FIG. 3) where wire strand 18 exits handle 50. If wire strand 18 exits handle 50 through slit 68, then incline 140 slants downward from channel 100 to slit 68. Alternatively, if wire strand 18 exits handle 50 through catch 66, then incline 140 slants upward from channel 100 to catch 66.

Figure 18:
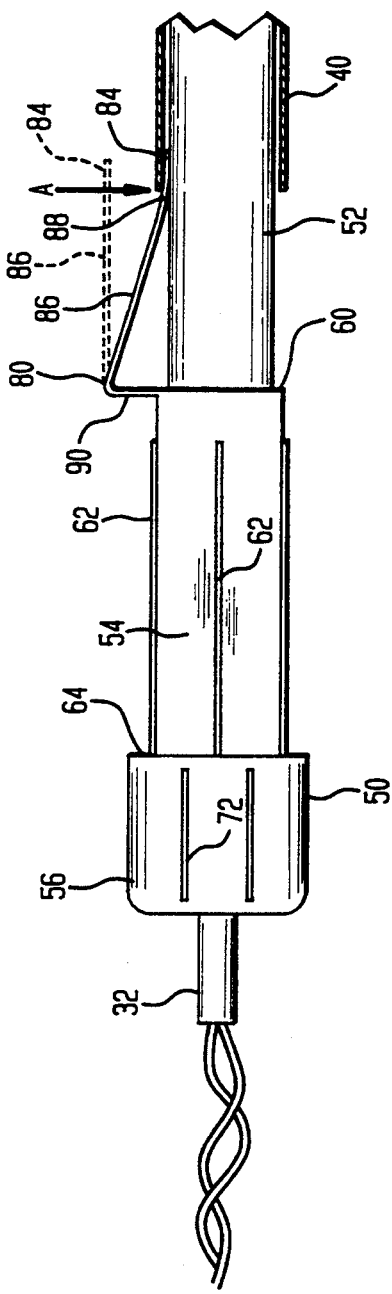
FIG. 18 is a side view of the handle of the fetal spiral electrode system in accordance with the present invention.

As shown in FIG. 18, handle 50 has three cylindrical sections: a forward section 52, a middle section 54, and a rearward section 56. A passage 58 extends through all three sections of handle 50 (see FIGS. 3 and 10). Passage 58 is about 4.5 mm in diameter at its top (in rearward section 56) and may taper to a narrower diameter to ensure that connector 32 fits snugly in passage 58.

Forward section 52 of handle 50 is integral with first region 102 of drive rod 30. Accordingly, forward section 52 provides a mounting end sized to be slidably received in the rearward end of guide tube 40. Middle section 54 of handle 50 has an outer diameter (7.1 mm or 0.28 inches) which is larger than the inner diameter of guide tube 40. Thus, middle section 54 provides a shoulder 60 to limit the forward movement of forward section 52 (and drive rod 30) inside guide tube 40. The respective lengths of drive rod 30, guide tube 40, and forward section 52 are selected so that spiral electrode 20 extends about 9 mm (0.35 inches) outside the forward end of guide tube 40 when forward section 52 is fully mounted inside the rearward end of guide tube 40 (such that shoulder 60 abuts the top of guide tube 40). Middle section 54 has ribs 62 to facilitate handling of drive mechanism 12 when attaching fetal spiral electrode 20 to the fetus.

Rearward section 56 of handle 50 is larger in diameter than middle section 54 and forms a shoulder 64. Like middle section 54, rearward section 56 of handle 50 has ribs 72 to facilitate handling. Passage 58 ends in a counterbore (about 5.5 mm in diameter) at the rearward end of rearward section 56.

As mentioned briefly above, two, alternative embodiments are shown by which wire strand 18 exits rearward section 56 of handle 50. The first embodiment is illustrated in FIGS. 3 and 4. Wire strand 18 travels in channel 100, up incline 140, and through catch 66. Wire strand 18 is fixed, by a wedging action, in position in catch 66. To remove wire strand 18 from drive mechanism 12, the user forces wire strand 18 out from catch 66 (against the wedging action) then wire strand 18 peels out of channel 100 as drive mechanism 12 is removed from guide tube 40.

The second embodiment by which wire strand 18 exits rearward section 56 of handle 50 is illustrated in FIGS. 10 and 11. Rearward section 56 has a slit 68, which is tapered into a V-shape, on the side of passage 58 opposite channel 100. Slit 68 is sized so that wire strand 18 can be forced downward through the wider bottom of V-shaped slit 68 into the narrower top of slit 68 to secure it when fetal spiral electrode system 10 is both packaged and in the initial stages of use.

Wire strand 18 travels in channel 100, down incline 140, and through slit 68. Wire strand 18 is fixed, by a wedging action; in position in slit 68. To remove wire strand 18 from drive mechanism 12, the user forces wire strand 18 out from slit 68 (against the wedging action) then wire strand 18 peels out of channel 100 as drive mechanism 12 is removed from guide tube 40.

By holding wires 26a and 26b in a fixed position, either in slit 68 or catch 66, holder 24 and electrodes 20 and 22 are held against the forward end of drive rod 30. Because holder 24 cannot move away from drive rod 30 while wires 26a and 26b are secured in slit 68 or catch 66, engagement is facilitated between fin-shaped reference electrode 22 and clutch 28 of drive mechanism 12 during implantation of fetal spiral electrode 20.

Handle 50 and drive rod 30 are molded together as part of integral drive mechanism 12. When the user rotates handle 50, therefore, drive rod 30 automatically rotates along with handle 50. Consequently, holder 24 and fetal spiral electrode 20 also rotate. The pressure fit of the conventional two-piece drive mechanism, which may inadequately transmit rotational motion between the handle and the drive tube (risking slippage), is avoided.

The integrally molded, single-piece drive mechanism 12 of the present invention provides the user with consistent and optimal tactile feedback. The user turns handle 50 until a mild resistance is felt. Such resistance indicates that fetal spiral electrode 20 has been securely attached to the fetus. Because there can be no slippage between handle 50 and drive rod 30, as is possible with the conventional two-piece drive mechanism, the user will receive the tactile feedback desired. Consequently, the user can be confident that a secure attachment of fetal spiral electrode 20 has been achieved.

Referring again to FIGS. 3 and 10, passage 58 is sized and tapered so that connector 32 may be wedged snugly within the walls of passage 58 (if catch 66 is provided as in FIG. 3) or between the wall of passage 58 and the electrode wires 26a and 26b (if slit 68 is provided as in FIG. 10), preventing movement of connector 32. Thus, connector 32 is protected from damage inside passage 58. In particular, ring contacts 34 and 36 are inside passage 58, protecting them during storage and handling.

6. Clip 80

As shown in FIGS. 5, 12, and 18, flexible safety clip 80 is integrally mounted to handle 50 at shoulder 60. Tail 84 of clip 80 is adapted to be wedged snugly between the inner diameter of guide tube 40 and the outer diameter of forward section 52 (which transitions to drive rod 30) of handle 50 during storage and handling of fetal spiral electrode system 10 before and during the initial stages of use.

Tail 84 is shown in the wedged position, the position in which fetal spiral electrode system 10 is stored before use, in FIG. 18. To wedge tail 84 between guide tube 40 and drive rod 30, starting from the position shown by the dashed lines in FIG. 18, tail 84 is pushed in the direction of arrow A into contact with drive rod 30 while guide tube 40 is pulled over tail 84.

Clip 80 has body 86 which is wider than tail 84. Body 86 is too wide to fit inside guide tube 40. Shoulder 88 on body 86 limits the distance by which clip 80 extends into guide tube 40. Thus, clip 80 maintains a predetermined distance between shoulder 64 of handle rearward section 56 and the rearward end of guide tube 40 during storage and initial use. The total length of clip 80 (about 13 mm or 0.5 inches) and the length of tail 84 (about 5 mm or 0.2 inches) assure that forward section 52 of handle 50 is not mounted completely inside the rearward end of guide tube 40 when clip 80 is wedged in position.

By maintaining this predetermined distance, drive rod 30 is retracted far enough inside guide tube 40 so that holder 24 and fetal spiral electrode 20 are retained in a protected position inside guide tube 40. Moreover, slit 68 or catch 66 secures wires 26a and 26b so that holder 24 is held against the forward end of drive rod 30. Because clip 80 is wedged between drive rod 30 and guide tube 40, relative motion between the two is effectively prevented and drive rod 30 cannot slip out of guide tube 40 accidentally during handling.

C. Use of the Present Invention

During storage, connector 32 is plugged into passage 58 in handle 50. Wire strand 18 is locked into catch 66 or slit 68. Safety clip 80 is wedged between guide tube 40 and drive rod 30, holding fetal spiral electrode 20 retracted in guide tube 40.

To use fetal spiral electrode system 10 of the present invention, the shape of guide tube 40 is adjusted and guide tube 40 is inserted through the mother's cervix and into contact with the fetus. Safety clip 80 is released by pulling handle 50 back slightly (about 10 mm or 0.4 inches) while holding guide tube 40 against the fetus. That action will remove tail 84 from between drive rod 30 and guide tube 40, once the end of tail 84 of clip 80 is pulled beyond guide tube 40, and tail 84 will spring open (in the direction opposite arrow A) into the position shown by dashed lines in FIG. 18.

In this position, tail 84 of clip 80 can be used as a pointer to inform the user when a complete rotation of fetal spiral electrode 20 has been achieved. Such indication minimizes the risk that fetal spiral electrode 20 will penetrate insufficiently or excessively into the fetal epidermis, which would occur upon insufficient or excessive rotation, respectively, of handle 50. If handle 50 is rotated more than about one or one and a quarter full turns, or beyond the point where slight resistance is felt (indicating that fetal spiral electrode 20 is properly secured to the fetus), fetal spiral electrode 20 may pull out of the fetal scalp tissue and, thus, damage it.

With tail 84 of clip 80 removed from engagement with guide tube 40, handle 50 can be used to push drive rod 30 through guide tube 40, without rotation, until fetal spiral electrode 20 contacts the fetus. Contact will occur just before the rearward end of guide tube 40 would contact shoulder 60 of handle 50. Clutch 28 engages fin-shaped reference electrode 22 and, accordingly, holder 24 and fetal spiral electrode 20 will move forward in guide tube 40 as drive rod 30 does so.

While pressure is maintained against the fetus with guide tube 40 and drive rod 30, drive rod 30 is rotated (in a clockwise direction), using handle 50, until fetal spiral electrode 20 is secured to the fetal epidermis. Typically, one full revolution (indicated when safety clip 80 returns to its original position) suffices to secure fetal spiral electrode 20.

Once fetal spiral electrode 20 is secured to the fetus, connector 32 is removed from passage 58. Such removal is facilitated by grip 44. Electrode wires 26a and 26b are released from catch 66 or slit 68 and are allowed to hang freely. Holding guide tube 40 against the fetus, the user slides drive mechanism 12 (including drive rod 30) completely out of guide tube 40 and out of the mother by pulling handle 50. There is no need to completely straighten wire strand 18 before drive mechanism 12 is removed. Wires 26a and 26b will automatically and laterally exit or peel away from channel 100 as drive mechanism 12 is pulled out. Subsequently, guide tube 40 is slid off electrode wires 26a and 26b, over connector 32, and out of the mother. This leaves electrodes 20 and 22, holder 24, and wires 26a and 26b in place inside the mother.

Finally, connector 32 is plugged into support plate 70 using grip 44. Connector 32 is pushed into support plate 70 until shoulder 46 contacts the surface of support plate 70, indicating that connector 32 is fully inserted. Insertion of connector 32 in support plate 70 connects electrodes 20 and 22 to monitor 78.

It will be understood by one skilled in the art that many variations of the embodiments described herein are contemplated. Although the invention has been described in terms of exemplary embodiments, it is contemplated that it may be practiced as outlined above with modifications within the spirit and scope of the appended claims.

What is claimed:

1. A fetal electrode product for transmitting signals indicative of fetal heart rate from a fetus to a monitor, said product comprising:
   a fetal spiral electrode, a maternal reference electrode, and a holder made of an insulating material, said electrodes mounted on opposite ends of said holder;
   a twisted wire strand including a pair of wires respectively connected to said fetal spiral electrode and said maternal reference electrode and adapted to connect said fetal spiral electrode and said maternal reference electrode to the monitor; and
   a drive mechanism connected to said holder when sliding and rotating said holder to secure attachment of said fetal spiral electrode to the fetus, said drive mechanism having:
   (a) a solid drive rod with a forward end, a rearward end, a region of smaller diameter having a diameter and a region of larger diameter having a diameter, said regions defining the torque versus angular deflection characteristics of said drive rod,
   (b) a handle connected to said rearward end of said drive rod and imparting translation and rotation to said drive rod, and
   (c) a clutch connected to said forward end of said drive rod and adapted to impart translation and rotation to said holder,
   each of said drive rod, said handle, and said clutch having a channel adapted to transport said twisted wire strand from said electrodes to the monitor and said region of smaller diameter having a plurality of journals spaced along its length, said journals having an outer diameter larger than the diameter of said region of smaller diameter, a notch corresponding to the width of said channel, and a height tangent to said twisted wire strand transported in said channel.

2. The fetal electrode product in accordance with claim 1 further comprising an annular guide tube having an inside diameter only slightly greater than the diameter of said region of larger diameter and adapted to be comfortably inserted through the cervix of a mother in labor, said guide tube slidably arranged around said drive rod.

3. The fetal electrode product in accordance with claim 2 wherein said drive rod has a third region with a diameter larger than the diameter of said region of smaller diameter and smaller than the diameter of said region of larger diameter.

4. The fetal electrode product in accordance with claim 1 further comprising an annular guide tube having an inside diameter and adapted to be comfortably inserted through the cervix of a mother in labor, said guide tube slidably arranged around said drive rod and said region of smaller diameter having a number of second journals spaced along its length with an outer diameter only slightly less than the inside diameter of said guide tube.

5. The fetal electrode product in accordance with claim 1 wherein said solid drive rod, said handle, and said clutch are integrally molded together to form said drive mechanism.

6. The fetal electrode product in accordance with claim 5 wherein said drive mechanism is formed from a polymer selected from the group consisting of polyethylene and polypropylene.

7. The fetal electrode product in accordance with claim 5 further comprising a ramp disposed between and connecting said drive rod and said clutch and an incline disposed between and connecting said drive rod and said handle.

8. The fetal electrode product in accordance with claim 1 wherein said twisted wire strand has an untwisted length.

9. The fetal electrode product in accordance with claim 1 wherein said clutch has a pair of arms defining a pair of slots releasably engaging and centering said maternal reference electrode for transmitting torque between said drive rod and said holder, said arms being pliable and slipping over said maternal reference electrode when said holder resists rotation.

10. A fetal electrode product for transmitting signals indicative of fetal heart rate from a fetus to a monitor, said product comprising:
   a fetal spiral electrode and a maternal reference electrode;
   a support plate adapted to be affixed to the mother and having a housing and first and second terminals within a socket opening in said housing, said first and second terminals adapted to be electrically connected to the monitor;
   a connector having:
   (a) a plug of a predetermined length with a first contact and a second contact spaced from each other and a tip and a rear, one of said contacts engaging one of said first and second terminals and the other of said contacts engaging the other of said first and second terminals when said connector is inserted fully into said socket opening of said support plate,
   (b) a grip of larger diameter than said plug arranged at said rear of said plug, and
   (c) a shoulder between said plug and said grip, said length of said plug predetermined so that said shoulder of said connector abuts said housing of said support plate when said connector is fully inserted into said socket opening; and
   a twisted wire strand including a pair of wires respectively connecting (a) one of said fetal spiral electrode and said maternal reference electrode to one of said first and said second contacts and (b) the other of said fetal spiral electrode and said maternal reference electrode to the second of said first and said second contacts.

11. The fetal electrode product in accordance with claim 10 further comprising:
   a holder made of an insulating material, said electrodes mounted on opposite ends of said holder; and
   a drive mechanism connected to said holder when sliding and rotating said holder to secure attachment of said fetal spiral electrode to the fetus, said drive mechanism having:
   (a) a solid drive rod with a forward end, a rearward end, a region of smaller diameter having a diameter and a region of larger diameter having a diameter, said regions defining the torque versus angular deflection characteristics of said drive rod,
   (b) a handle connected to said rearward end of said drive rod and imparting translation and rotation to said drive rod, and
   (c) a clutch connected to said forward end of said drive rod and adapted to impart translation and rotation to said holder,
   each of said drive rod, said handle, and said clutch having a channel adapted to transport said twisted wire strand from said electrodes to said connector.

12. The fetal electrode product in accordance with claim 11 wherein said region of smaller diameter has a plurality of journals spaced along its length, said journals having an outer diameter larger than the diameter of said region of smaller diameter, a notch corresponding to the width of said channel, and a height tangent to said twisted wire strand transported in said channel.

13. The fetal electrode product in accordance with claim 12 further comprising an annular guide tube having an inside diameter only slightly greater than the diameter of said region of larger diameter and adapted to be comfortably inserted through the cervix of a mother in labor, said guide tube slidably arranged around said drive rod.

14. The fetal electrode product in accordance with claim 13 wherein said drive rod has a third region with a diameter larger than the diameter of said region of smaller diameter and smaller than the diameter of said region of larger diameter.

15. The fetal electrode product in accordance with claim 12 further comprising an annular guide tube having an inside diameter and adapted to be comfortably inserted through the cervix of a mother in labor, said guide tube slidably arranged around said drive rod and said region of smaller diameter having a number of second journals spaced along its length with an outer diameter only slightly less than the inside diameter of said guide tube.

16. The fetal electrode product in accordance with claim 11 wherein said solid drive rod, said handle, and said clutch are integrally molded together to form said drive mechanism.

17. The fetal electrode product in accordance with claim 16 wherein said drive mechanism is formed from a polymer selected from the group consisting of polyethylene and polypropylene.

18. The fetal electrode product in accordance with claim 16 further comprising a ramp disposed between and connecting said drive rod and said clutch and an incline disposed between and connecting said drive rod and said handle.

19. The fetal electrode product in accordance with claim 11 wherein said twisted wire strand has an untwisted length.

20. The fetal electrode product in accordance with claim 11 wherein said clutch has a pair of arms defining a pair of slots releasably engaging and centering said maternal reference electrode for transmitting torque between said drive rod and said holder, said arms being pliable and slipping over said maternal reference electrode when said holder resists rotation.

21. A fetal electrode product for transmitting signals indicative of fetal heart rate from a fetus to a receiver, said product comprising:
   an unslotted annular guide tube having an inside diameter and adapted to be comfortably inserted through the cervix of a mother in labor;
   a fetal spiral electrode, a maternal reference electrode, and a holder slidably and rotatably disposed in said guide tube and made of an insulating material, said electrodes mounted on opposite ends of said holder;

a drive mechanism connected to said holder when sliding and rotating said holder to secure attachment of said fetal spiral electrode to the fetus, said drive mechanism having:
  (a) a solid drive rod with an outside diameter, a forward end and a rearward end,
  (b) a handle connected to said rearward end of said drive rod and imparting translation and rotation to said drive rod, and
  (c) a clutch connected to said forward end of said drive rod and adapted to impart translation and rotation to said holder,
said drive mechanism having a channel longitudinally disposed in each of said drive rod, said handle, and said clutch;
a connector having an outside dimension at least equal to said outside diameter of said solid drive rod to facilitate handling and smaller than said inside diameter of said annular guide tube so that said guide tube can be pulled over said connector after said fetal spiral electrode is attached to the fetus, said connector including at least two contacts separated and electrically isolated from each other for transmitting said signals to said receiver; and
a twisted wire strand including a pair of wires respectively connecting (a) one of said fetal spiral electrode and said maternal reference electrode to one of said contacts and (b) the other of said fetal spiral electrode and said maternal reference electrode to the second of said contacts, said twisted wire strand disposed along said channel of said drive mechanism.

22. The fetal electrode product in accordance with claim 21 wherein said drive rod has a region of smaller diameter having a diameter and a region of larger diameter having a diameter, said regions defining the torque versus angular deflection characteristics of said drive rod.

23. The fetal electrode product in accordance with claim 22 wherein said region of smaller diameter has a plurality of journals spaced along its length, said journals having an outer diameter larger than the diameter of said region of smaller diameter, a notch corresponding to the width of said channel, and a height tangent to said twisted wire strand transported in said channel.

24. The fetal electrode product in accordance with claim 23 wherein the diameter of said region of larger diameter is only slightly less than the inside diameter of said guide tube.

25. The fetal electrode product in accordance with claim 24 wherein said drive rod has a third region with a diameter larger than the diameter of said region of smaller diameter and smaller than the diameter of said region of larger diameter.

26. The fetal electrode product in accordance with claim 23 wherein said region of smaller diameter has a number of second journals spaced along its length with an outer diameter only slightly less than the inside diameter of said guide tube.

27. The fetal electrode product in accordance with claim 22 wherein said solid drive rod, said handle, and said clutch are integrally molded together to form said drive mechanism.

28. The fetal electrode product in accordance with claim 27 wherein said drive mechanism is formed from a polymer selected from the group consisting of polyethylene and polypropylene.

29. The fetal electrode product in accordance with claim 27 further comprising a ramp disposed between and connecting said drive rod and said clutch and an incline disposed between and connecting said drive rod and said handle.

30. The fetal electrode product in accordance with claim 22 wherein said twisted wire strand has an untwisted length.

31. The fetal electrode product in accordance with claim 32 wherein said clutch has a pair of arms defining a pair of slots releasably engaging and centering said maternal reference electrode for transmitting torque between said drive rod and said holder, said arms being pliable and slipping over said maternal reference electrode when said holder resists rotation.

32. A fetal electrode product for transmitting signals indicative of fetal heart rate from a fetus to a monitor, said product comprising:
an unslotted annular guide tube having an inside diameter and adapted to be comfortably inserted through the cervix of a mother in labor;
a fetal spiral electrode, a maternal reference electrode, and a holder slidably and rotatably disposed in said guide tube and made of an insulating material, said electrodes mounted on opposite ends of said holder;
a support plate adapted to be affixed to the mother and having a housing and first and second terminals within a socket opening in said housing, said first and second terminals adapted to be electrically connected to the monitor;
a drive mechanism connected to said holder when sliding and rotating said holder to secure attachment of said fetal spiral electrode to the fetus, said drive mechanism having:
  (a) a solid drive rod with an outside diameter, a forward end, a rearward end, and at least two regions of different diameter, said regions defining the torque versus angular deflection characteristics of said drive rod,
  (b) a handle connected to said rearward end of said drive rod and imparting translation and rotation to said drive rod, and
  (c) a clutch connected to said forward end of said drive rod and adapted to impart translation and rotation to said holder,
said drive mechanism having a channel longitudinally disposed in each of said drive rod, said handle, and said clutch;
a connector having:
  (a) a plug of a predetermined length with a first contact and a second contact spaced from each other and a tip, one of said contacts engaging one of said first and second terminals and the other of said contacts engaging the other of said first and second terminals when said connector is inserted fully into said socket opening of said support plate,
  (b) a grip with a diameter larger than said plug, greater than said outside diameter of said solid drive rod to facilitate handling, and smaller than said inside diameter of said annular guide tube so that said guide tube can be pulled over said connector after said fetal spiral electrode is attached to the fetus, and
  (c) a shoulder between said plug and said grip, said length of said plug predetermined so that said shoulder of said connector abuts said housing of said support plate when said connector is fully inserted into said socket opening; and a twisted wire strand including a pair of wires respectively connecting (a) one of said fetal spiral electrode and said maternal reference electrode to one of said contacts and (b) the other of said fetal spiral electrode and said maternal reference electrode to the second of said contacts, said twisted wire strand disposed along said channel of said drive mechanism.

* * * * *

UNITED STATES PATENT AND TRADEMARK OFFICE
CERTIFICATE OF CORRECTION

PATENT NO.    : 5,388,579
DATED         : February 14, 1995
INVENTOR(S)   : Edward Dowd et al.

It is certified that error appears in the above-identified patent and that said Letters Patent is hereby corrected as shown below:

Title page, item [57]:
In the Abstract, line 9, delete "rods" and insert
--rod,--;

Column 1, line 62, delete "Nos." and insert --No.--;

Column 4, line 16, delete "handled" and insert
--handle,--.;

Column 11, line 37, delete "designs" and insert
--design,--; and

In claim 31, at Column 20, line 10, delete "32" and insert
--22--.

Signed and Sealed this

Eighteenth Day of April, 1995

Attest:

BRUCE LEHMAN

*Attesting Officer*

*Commissioner of Patents and Trademarks*